United States Patent [19]

Curtis et al.

[11] Patent Number: 4,774,078

[45] Date of Patent: Sep. 27, 1988

[54] STABLE ANTIPLAQUE DENTIFRICE BASED ON HEXETIDINE, ZINC ION AND FLUORIDE

[75] Inventors: John P. Curtis, Piscataway; Shamsul K. Bakar, New Brunswick; John J. Donohue, Neshanic; Richard J. Crawford, Asbury; Kathleen M. Yuhasz-Kotarsky, Fords; John M. Coviello, Jr., Somerset, all of N.J.

[73] Assignee: Colgate-Palmolive Company, New York, N.Y.

[21] Appl. No.: 915,475

[22] Filed: Oct. 6, 1986

[51] Int. Cl.$^4$ ............................................. A61K 7/18
[52] U.S. Cl. .................................. 424/52; 424/49; 424/54; 424/145; 514/835
[58] Field of Search ................. 424/49, 52, 54, 145; 514/835

[56] References Cited

U.S. PATENT DOCUMENTS

| 4,490,353 | 12/1984 | Crawford et al. | 424/54 |
| 4,522,806 | 6/1985 | Muhlemann et al. | 424/54 |
| 4,528,182 | 7/1985 | Curtis et al. | 424/54 |

OTHER PUBLICATIONS

Saxer et al., *Chem. Abst.*, 99, 372 (1983) 99:218429n.

*Primary Examiner*—J. R. Brown
*Assistant Examiner*—F. T. Moezie
*Attorney, Agent, or Firm*—Robert L. Stone; Murray M. Grill

[57] ABSTRACT

A cosmetically and therapeutically stable antiplaque dentifrice comprising a combination of hexetidine, a soluble zinc salt and a fluoride compound capable of providing a fluoride ion, as the antiplaque agent in dental vehicle containing a polyethylene glycol humectant and a dental abrasive.

14 Claims, No Drawings

STABLE ANTIPLAQUE DENTIFRICE BASED ON HEXETIDINE, ZINC ION AND FLUORIDE

FIELD OF THE INVENTION

This invention relates to a cosmetic and therapeutic stable antiplaque dentifrice containing the synergistic antibacterial combination of hexetidine, a zinc salt, a fluoride-providing compound, a surfactant particularly selected from the group consisting of an anionic, nonionic, zwitterionic detergent or a mixture thereof, a polyethylene glycol humectant, a nonionic gelling agent and a compatible dental abrasive, and having a pH of about 5-6.

BACKGROUND OF THE INVENTION

Hexetidine, which is an amino-hexahydro-pyrimidine derivative, is a broad-spectrum antibacterial, and has been formulated in a number of products including mouthrinses (Oraldene, Sterisil) and dentifrices (Mentadent-P). U.S. Pat. No. 2,837,463 discloses therapeutic compositions, including mouthwashes and dentifrices, containing said hexahydropyrimidine antibacterial compounds. British Pat. No. 771,768 also discloses dental therapeutic compositions containing a 5-methyl-5-amino-hexahydropyrimidine compound, said dental compositions including pastes, powders, liquids, chewing gums, tablets, lozenges and troches.

The 5-aminohexahydropyrimidines and a process for their preparation is disclosed in U.S. Pat. No. 2,387,043 which is incorporated herein by reference.

The use of hexetidine (5-amino-1,3-bis(2-ethylhexyl)-5-methyl-hexahydropyrimidine) as an optional antibacterial additive in oral compositions is known in the prior art as disclosed in U.S. Pat. Nos. 3,622,661; 3,984,537; 3,989,814; 4,490,353; 4,528,182; and in British Pat. No. 1,533,634 and No. 1,461,896.

U.S. Pat. No. 4,522,806, European Patent Application No. 049,830 and British Pat. No. 2,084,870 disclose oral compositions containing hexetidine, and zinc salts for the inhibition of dental plaque without staining the teeth in an aqueous oral vehicle containing glycerin and optionally, a fluoride compound.

However, attempts to formulate a stable antiplaque dentifrice based on these ingredients using glycerin, the most common dentifrice humectant, have been unsuccessful. Glycerin formulations were soft, and separated during the accelerated aging tests. It has been found that when a polyethylene glycol humectant is used, formulations can be prepared which are cosmetically stable and successfully pass the accelerated aging tests.

Furthermore, it has been difficult to formulate a dentifrice containing hexetidine (5-amino-1,3-bis(2-ethyl hexyl)-5-methyl-hexahydropryrimidine), zinc ($Zn++$), and fluoride ($F-$) in which available hexetidine is minimally inactivated or decomposed, and soluble zinc ($Zn++$) or fluoride ($F-$) is minimally complexed or lost, due to interaction with formula ingredients. In order to overcome this problem, it has been found that by combining a surfactant selected from the group consisting of anionic, nonionic, zwitterionic or mixtures thereof as the solubilizer for the water insoluble hexetidine, employing as humectant a polyethylene glycol, using a nonionic gelling agent such as hydroxy ethyl cellulose, combining a compatible dental abrasive, preferably hydrated alumina, calcined alumina or hydrous silica gel, and maintaining a pH below about 6, and preferably between 5 and 6, preserves and enhances the antimicrobial activity of the hexetidine in combination with the soluble zinc salts ($Zn++$) and the fluoride ($F-$) in the dentifrice.

The prior art does not disclose a cosmetically and therapeutically antiplaque dentifrice containing as the essential ingredients an antimicrobial combination of hexetidine, a zinc salt and a fluoride-providing compound; a surfactant; a polyethylene glycol humectant; a nonionic gelling agent; and a compatible dental abrasive, and said dentifrice having a pH below about 6.

SUMMARY OF THE INVENTION

It has now been found that dentifrice formulations such as dental cream and toothpaste containing the antimicrobial combination of hexetidine, a zinc salt and a fluoride compound effective as an antiplaque agent, may be therapeutically stabilized against deactivation of antimicrobial activity, as well as cosmetically stabilized against separation of ingredients and phase separation during aging, by the combined use of a surfactant with a compatible dental abrasive, a polyethylene glycol humectant, a nonionic gelling agent (e.g. hydroxyethylcellulose), and maintaining said formulation at a pH of about 5-6.

Accordingly, a primary object of present invention is to provide a cosmetically stable antiplaque and antigingivitis dentifrice based on the combination of hexetidine, zinc salt, and a fluoride containing a polyethylene glycol humectant.

Another object of the present invention is to provide a therapeutically stable antiplaque dentifrice based on the antibacterial combination of hexetidine, $Zn++$ and $F-$, containing an anionic, nonionic or zwitterionic surfactant, a nonionic gelling agent, and having a pH up to about 6 and preferably about 5-6.

Still another object of the present invention is to provide a stable antiplaque dentifrice based on the antibacterial combination of hexetidine, $Zn++$ and $F-$, containing as the essential ingredients, a compatible dental abrasive such as calcined alumina, hydrated alumina or hydrous silica gel, a polyethylene glycol humectant, a nonionic gelling agent, such as hydroxyethyl cellulose and a surfactant particularly selected from the group consisting of anionic, nonionic and zwitterionic detergents.

Another object of the present invention is to reduce or eliminate possible side effects, such as staining of teeth and a bitter taste, by using low levels of hexetidine in the dentifrice.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention as embodied and broadly described herein, the stable antiplaque dentifrice of this invention comprises as the essential ingredients an effective antibacterial amount of the combination of hexetidine, a zinc salt and a fluoride-providing compound, a surfactant, a nonionic gelling agent, a polyethylene glycol humectant and a compatible dental abrasive, and having an acid pH up to about 6.

More specifically, present invention relates to a stable antiplaque dentifrice comprising the combination of low levels of hexetidine of about 0.1–0.75% by weight, about 0.1–5% of a zinc salt and about 0.05–2% of a fluoride-providing compound as the antibacterial and anticaries agents, about 20–30% of a polyethylene glycol humectant, about 0.5–5% of a nonionic gelling agent, about 0.5–5% of a surfactant selected from the group consisting of anionic, nonionic and zwitterionic detergent, and about 40–60% of a compatible dental abrasive, said composition having an acid pH up to 6 and preferably about 5–6.

Hexetidine is a broad-spectrum, water-insoluble antibacterial, having the chemical formula

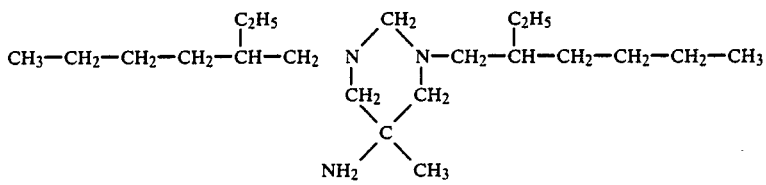

5-amino-1,3-bis(2 ethylhexyl)-5-methyl-hexahydropyrimidine. It has been used as an antibacterial agent in antiplaque and antigingivitis oral compositions as previously discussed. However, hexetidine is a bitter-tasting chemical, thereby limiting its use to low levels in order to minimize its bitter taste, which in turn limits its therapeutic activity. However, low levels of hexetidine, in the order of about 0.1–0.75% by weight, in combination with water soluble zinc salts in amounts of about 0.1–1.7% by weight, provide synergistically increased antimicrobial activity, as shown in Table I when tested against *Strep mutans*, the bacteria found in dental plaque.

The combination of hexetidine with a zinc salt as an antiplaque agent in oral compositions is disclosed in U.S. Pat. No. 4,522,806 and European Pat. No. 049,830, which is incorporated herein by reference. The zinc salt in the antibacterial combination with hexetidine may be any water soluble zinc salt such as zinc chloride, zinc acetate, zinc sulfate, and the like. Zinc fluoride and zinc citrate are less soluble, but also may be used.

Table I gives the MIC (minimum inhibitory concentration) results with *Strep. mutans*.

All the active ingredients (AI) are in water/alcohol/propylene glycol mixtures.

TABLE I

| Active Ingredient | ppm | Ratio | MIC, ppm | FIC Index |
|---|---|---|---|---|
| Hexetidine/zinc++ | 150/150 | 1:1 | .12/.12 | 0.20 |
| Hexetidine | 750 | — | .60 | — |
| Zinc++ | 750 | — | 40.00 | — |

The lower MIC value (0.12 ppm) is indicative of greater antibacterial activity. The FIC (Fractional Inhibitory Concentration), has been calculated from the MIC data for each ratio.

The MIC results show that the antimicrobial activity of the combination is not the sum total of the individual components' antibacterial activity, but is a synergistically more effective antibacterial agent at lower concentrations. A minimum concentration of 0.60 ppm hexetidine alone is needed for total bacterial inhibition, and a minimum concentration of 40 ppm of zinc++ alone is required for total bacterial inhibition; whereas a concentration of 0.12 ppm hexetidine in combination with 0.12 ppm zinc++ effects total bacterial inhibition.

This increase in the antibacterial activity of the hexetidine due to the presence of the zinc++ reduces the amount necessary to produce a therapeutic effect, and this minimizes the bitter taste associated with hexetidine.

The third member of the antibacterial combination is a fluoride-providing compound characterized by the ability to release fluoride ions in water and by substantial freedom from reaction with other compounds of the dentifrice. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal fluorides, such as sodium and potassium fluorides, sodium monofluorophosphate and mixtures thereof, are preferred. When the fluoride-providing compound is zinc fluoride, the fluoride providing compound and the zinc salt of the present invention are one and the same.

The amount of fluoride-providing compounding is dependent to some extent, upon the type of compound, its solubility, and the dentifrice, but it must be a nontoxic amount. In a solid oral preparation, such as a toothpaste or dental cream, an amount of such compound which releases a maximum of 1% by weight of the preparation is considered satisfactory. Any suitable minimum amount of such compound may be used, but it is preferably to employ sufficient compound to release from 0.005% to 1%, and preferably about 0.1% of fluoride ion. Typically, in the cases of alkali metal fluorides, this component is present in an amount up to 2% by weight, based on the weight of the preparation, and preferably in the range of from 0.5% to 1%. In the case of sodium monofluorophosphate, the compound may be present in an amount up to 7.6% by weight, more typically 0.76%.

In addition, it has been found that the pH of this dentifrice system should be maintained below 6, and preferably between 5 and 6 in order to preserve the reactivity of the zinc ion and hexetidine in the dentifrice. The pH of the dentifrice can be adjusted to 5–6 with an appropriate acid such as acetic acid, citric acid, hydrochloric acid, phosphoric acid, etc., if necessary. The availability of the zinc ion, hexetidine, and fluoride has been demonstrated by in vitro tests on dentifrice formulations that have satisfactorily completed the accelerated aging tests.

The dentifrice in accordance with the invention may be in the form of a toothpaste, dental cream or a gel containing a compatible dental polishing agent of abrasive wherein the liquid vehicle may comprise water, typically in an amount of about 10–35% by weight of the composition; and a polyethylene glycol as the humectant in an amount of about 20-30% by weight. The polyethylene glycol humectants of present invention have an average molecular weight up to 1000, e.g., about 200-1000, preferably about 400-800, and most preferably about 550-650. These products are obtainable from the Union Carbide Chemicals Company as Carbowax-600, Carbowax-400, etc., and are readily miscible with water. Particularly advantageous liquid ingredients comprise mixtures of water with polyethylene glycol.

A nonionic gelling agent (thickening agent) including natural or synthetic gums such as hydroxyethyl cellulose, hydroxymethyl cellulose, methyl cellulose and the like may be used, in the range of about 0.5-5% by weight. The preferred gelling agent is hydroxyethyl cellulose.

In a toothpaste, dental cream or gel, the liquids and solids are proportioned to form a creamy or gelled mass which is extrudable from a pressurized container or from a collapsible tube.

An essential ingredient in present stable dentifrice is a surface active agent particularly selected from the group consisting of an anionic, nonionic or zwitterionic detergent, in amounts of about 0.5-5% by weight. The surfactant is compatible with the antibacterial combination of hexetidine, zinc salt and fluoride compound; solubilizes the hexetidine ingredient; does not react with the zinc salt or other components of said antibacterial combination; or deactivate the hexetidine.

Suitable anionic detergents are water-soluble salts of higher fatty acid monoglyceride monosulphates, such as the sodium salt of the monosulphated monoglyceride of hydrogenated coconut oil fatty acids; higher alkyl sulphates, such as sodium lauryl sulphate, alkyl aryl sulphonates, such as sodium dodecyl benzene sulphonate, higher alkyl sulphoacetates; higher fatty acid esters of 1,2-dihydroxy propane sulphonates; and substantially saturated higher aliphatic acyl amides of lower aliphatic amino carboxylic acids such as those having 12 to 16 carbons in the fatty acid, alkyl or acyl radicals. Examples of the last mentioned amides are N-lauroyl sarcosine, and the sodium, potassium, and ethanolamide salts of N-lauroyl, N-myristoyl or N-palmitoyl sarcosine.

Nonionic surface active agents include condensates of sorbitan monostearate with approximately 20-60 moles of ethylene oxides (e.g. "Tweens") such as polyoxyethylene (20) sorbitan monoisostearate or polyoxyethylene (40) diisostearate; condensates of ethylene oxide with propylene oxide condensates of propylene glycol ("Pluronics"); condensates of higher fatty alcohols or ethers with ethylene oxide; condensates of alkyl thiophenols with 10 to 15 ethylene oxide units; and ethylene oxide addends of monoesters of hexahydric alcohols and inner esters thereof such as sorbitan monolaurate, sorbitol monooleate, mannitan monopalmitate, and sorbitan monisostearate.

Zwitterionic surface active agents include the betaines and sulfobetaines. Typical alkyl dimethyl betaines include decyl betaine or 2-(N-decyl-N,N-dimethylammonio)acetate, coco betaine, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like. These sulfo-betaines are similar in structure to the betaines, but have a sulfonate group in place of the carboxylate group, and include alkylsulfobetaines, alkylamidosulfobetaines and alkylaminosulfobetaines.

Another essential ingredient in present dentifrice formulations is the use of the polyethylene glycol as the sole humectant in order to afford cosmetic (physical) stability to the composition. Glycerin, the most common dentifrice humectant can be incompatible with the antibacterial combination of hexetidine/zinc salt/fluoride and exhibits phase separation during the accelerated aging tests. The polyethylene glycol humectant constitutes about 20-30% by weight of the formulation.

Another essential ingredient in present dentifrice is a gelling agent which is a nonionic gum, in an amount up to 5% by weight and preferably about 0.5-3%. It has been found that large organic anionic molecules such as carboxymethylcellulose have the potential to deactivate the antibacterial activity. Accordingly, hydroxyethylcellulose, which is a nonionic organic molecule, is the preferred gelling agent. Other nonionic gelling agents may be used such as hydroxymethylcellulose, and the like.

Another essential ingredient in present dentifrice is a water-insoluble dental abrasive or polishing material, which is compatible with the formulation. The abrasive or polishing agent constitutes about 40-60% by weight of the dentifrice composition. Suitable polishing agents include hydrated alumina, calcined alumina, silica, including acid, neutral and alkaline silica, hydrous silica gel, dihydrated dicalcium phosphate, sodium or potassium metaphosphate, tricalcium phosphate and other phosphate salts, calcium carbonate, aluminum silicate, zirconium silicates, plastics such as polymethacrylate, bentonite and mixtures thereof. Preferred polishing materials include calcined alumina, hydrated alumina and hydrous silica gel.

It has been found that only by utilizing the specific combination of ingredients of surfactant, polyethylene glycol, nonionic gelling agent, and a compatible abrasive, can a stable antiplaque dentifrice based on the antibacterial combination of hexetidine/zinc salts/fluoride, be obtained.

Various other materials may be incorporated in the oral preparations of the invention, including coloring or whitening agents, such as titanium dioxide, preservatives, perfumes, flavoring agents and sweeteners and mixtures thereof and acidifying agents, in minimal amounts up to 5% by weight, preferably up to 1%, provided they do not adversely affect the antibacterial properties and stability properties of present novel dentifrice composition. Desirably the flavoring agent is principally flavor oil such as peppermint, spearmint and mixture thereof.

The dentifrice composition of this invention is prepared by conventional methods of making toothpastes, dental creams and gels. More specifically, a toothpaste or dental cream may be prepared by dispersing a gelling agent in a liquid (humectant and/or water), adding to and mixing with said dispersion an aqueous solution of water-soluble ingredients such as fluorides, zinc salts, saccharin and the like, followed by the addition with mixing of the polishing agent, and lastly admixing the surfactant, the hexetidine and flavor, and tubing or otherwise packaging the final composition.

In the practice of this invention, to promote oral hygiene, the dentifrice composition according to this invention is applied regularly to dental enamel by brushing the teeth for 30-90 seconds at least once a day.

DETAILED DESCRIPTION OF THE INVENTION

The following examples are merely illustrative of the invention, but it is understood that the invention is not limited thereto. All amounts of various ingredients are by weight unless otherwise specified.

| Examples 1 and 2 Dental Cream | | |
|---|---|---|
| | Parts | |
| Ingredients | 1 | 2 |
| Hexetidine | 0.20 | 0.20 |
| Zinc Acetate Dihydrate | 0.67 | |
| Zinc Chloride | | 0.42 |
| Sodium Fluoride | 0.22 | 0.22 |
| Sodium Lauryl Sulfate | 1.20 | 1.20 |
| Polyethylene Glycol | 25.00 | 25.00 |
| Hydrated Alumina | 42.00 | 42.00 |
| Calcined Alumina | 10.00 | 10.00 |
| Hydroxyethyl Cellulose | 1.40 | 1.40 |
| Flavor | 1.00 | 1.00 |
| Sodium Saccharin | 0.30 | 0.30 |
| Deionized Water, q.s. to | 100.00 | 100.00 |

These dentifrices are made by adding an aqueous solution of sodium saccharin, sodium fluoride and zinc chloride or zinc acetate to the dispersion of hydroxy ethyl cellulose in polyethylene glycol-600 and mixing for about half an hour. This mixture is added to a mixture of hydrated alumina and calcined alumina, and mixed for about 20 minutes under vacuum. The sodium lauryl sulfate, flavor and hexetidine are added thereto and mixed for another 10 minutes under vacuum. The pH of the final product is adjusted to 5-6 with hydrochloric acid.

The dentifrices are antimicrobially active and after aging 9 weeks at 49° C. are cosmetically stable and have the following active ingredient stabilities:

| Active Ingredient | % Available After Aging |
|---|---|
| Available Hexetidine | 65% |
| Water Soluble Zinc (Zn++) | 60% |
| Water Soluble Fluoride (F−) | 67% |

| Examples 3 and 4 Dental Cream | | |
|---|---|---|
| | Parts | |
| Ingredients | 3 | 4 |
| Hexetidine | 0.75 | 0.75 |
| Zinc Acetate Dihydrate | 1.68 | |
| Zinc Chloride | | 1.04 |
| Sodium Fluoride | 0.22 | 0.22 |
| Polyoxyethylene (20) Sorbitan Monoisostearate | 1.00 | 1.00 |
| Polyethylene Glycol-600 | 20.00 | 25.00 |
| Hydrated Alumina | 42.00 | 42.00 |
| Calcined Alumina | 10.00 | 10.00 |
| Hydroxyethyl Cellulose | 1.20 | 1.40 |
| Flavor | 1.00 | 1.00 |
| Sodium Saccharin | 0.30 | 0.30 |
| Deionized Water, q.s. to | 100.00 | 100.00 |

The pH is adjusted to 5.0–6.0 with hydrochloric acid.

Examples 3 and 4 are similarly prepared in accordance with the method used in Examples 1 and 2. The dentifrices are antimicrobially active and after aging 9 weeks at 49° C. are cosmetically stable and have the following active ingredient stabilities:

| Active Ingredient | % Available After Aging |
|---|---|
| Available Hexetidine | 92% |
| Water Soluble Zinc (Zn++) | 84% |
| Water Soluble Fluoride (F−) | 60% |

| Example 5 Dental Cream | |
|---|---|
| Ingredient* | Parts |
| Hydroxyethylcellulose | 1.40 |
| Sodium Fluoride | 0.22 |
| Sodium Saccharin | 0.20 |
| Polyethylene Glycol 600 | 21.00 |
| Titanium Dioxide | 0.40 |
| Zinc Acetate.2H$_2$O | 1.00 |
| Hexetidine | 0.32 |
| Hydrated Alumina | 50.00 |
| Cocoamidopropyl Betaine (30%) | 1.00 |
| Water, q.s. to | 100.00 |

*pH is adjusted to 5.5 with hydrochloric acid if necessary.

| Example 6 | |
|---|---|
| Ingredients | Percent |
| Hexetidine | 0.2 |
| Polyethylene glycol-600 | 20.0 |
| Hydroxyethylcellulose | 1.3 |
| *H$_2$O, ZnF$_2$, Acid Sacch. (pH 4.35) | 29.6 |
| Hydrated Alumina | 47.5 |
| Polyoxyethylene (20) sorbitan monoisostearate | 1.0 |
| TiO$_2$ | 0.1 |
| Water, q.s. to | 100.00 |
| pH is 5.6 | |

*Aqueous solution containing 0.2% acid saccharin 0.4% ZnF$_2$(0.1% F−).
1500 ppm Zn++
1000 ppm F−

Variations in the above formulations may be made. For example, other polishing agents such as hydrous silica gel may be substituted for the specific polishing agents in the examples. Similarly other anionic, nonionic or zwitterionic surfactants may be substituted for the specific surfactants in the Examples.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A stable antiplaque dentifrice composition consisting essentially of the antimicrobial combination of about 0.1–0.75% by weight of hexetidine, about 0.1–5% by weight of a water soluble zinc salt and a fluoride-providing compound selected from the group consisting of alkali, alkaline earth metal and heavy metal fluoride salts in an amount which releases about 0.005–1% fluoride ion; about 0.5–5% by weight of a surfactant selected from the group consisting of anionic, nonionic, and zwitterionic detergents; about 0.5–5% by weight of a nonionic natural or synthetic gum gelling agent, about 20–30% by weight of a polyethylene glycol as the sole humectant having an average molecular weight of about 200 to about 1000; about 40–60% by weight of a water insoluble dental abrasive, said composition having a pH of about 5–6.

2. The dentifrice according to claim 1, wherein the dental abrasive is a mixture of hydrated alumina and calcined alumina.

3. The dentifrice according to claim 1, wherein the dental polishing agent is hydrated alumina.

4. The dentifrice according to claim 1, wherein the gelling agent is hydroxyethyl cellulose, in an amount of about 0.5-5% by weight.

5. The dentifrice according to claim 1 wherein the nonionic surfactant is selected from the group consisting of polyoxyethylene (20) sorbitan monoisostearate and polyoxyethylene (40) sorbitan diisostearate.

6. The dentifrice according to claim 1, wherein the anionic surfactant is sodium lauryl sulfate.

7. The dentifrice according to claim 1, wherein the zwitterionic surfactant is cocoamidopropyl betaine.

8. The dentifrice according to claim 1, wherein the zinc salt is zinc acetate.

9. The dentifrice according to claim 1, wherein the zinc salt is zinc chloride.

10. The dentifrice according to claim 1, wherein the zinc salt and the fluoride providing compound is zinc fluoride.

11. The dentifrice according to claim 1, wherein the humectant is a polyethylene glycol having an average molecular weight of about 400-800.

12. The dentifrice according to claim 1, wherein the humectant is a polyethylene glycol having an average molecular weight of about 550-650.

13. The dentifrice according to claim 1, wherein the zinc salt is water soluble and constitutes about 0.1-1.7% by weight of the composition.

14. The dentifrice according to claim 1, containing 0.76-7.6% by weight of sodium monofluorophosphate.

* * * * *